United States Patent
Himmler et al.

(10) Patent No.: US 10,011,557 B2
(45) Date of Patent: Jul. 3, 2018

(54) METHOD FOR PRODUCING BIPHENYLAMINES FROM AZOBENZENES BY RUTHENIUM CATALYSIS

(71) Applicant: BAYER CROPSCIENCE AKTIENGESELLSCHAFT, Monheim am Rhein (DE)

(72) Inventors: Thomas Himmler, Odenthal (DE); Lars Rodefeld, Leverkusen (DE); Jonathan Hubrich, Göttingen (DE); Lutz Ackermann, Göttingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/523,038

(22) PCT Filed: Nov. 2, 2015

(86) PCT No.: PCT/EP2015/075368
§ 371 (c)(1),
(2) Date: Apr. 28, 2017

(87) PCT Pub. No.: WO2016/071249
PCT Pub. Date: May 12, 2016

(65) Prior Publication Data
US 2017/0334832 A1 Nov. 23, 2017

(30) Foreign Application Priority Data
Nov. 3, 2014 (EP) .................................... 14191403

(51) Int. Cl.
C07C 209/42 (2006.01)
C07C 213/02 (2006.01)
C07C 227/04 (2006.01)
C07C 211/45 (2006.01)
C07C 229/52 (2006.01)
C07C 245/08 (2006.01)

(52) U.S. Cl.
CPC .......... *C07C 209/42* (2013.01); *C07C 211/45* (2013.01); *C07C 213/02* (2013.01); *C07C 227/04* (2013.01); *C07C 229/52* (2013.01); *C07C 245/08* (2013.01)

(58) Field of Classification Search
CPC .................................................. C08C 209/42
See application file for complete search history.

(56) References Cited

U.S. PATENT DOCUMENTS

| 7,329,633 B2 | 2/2008 | Dunkel et al. |
| 7,521,397 B2 | 4/2009 | Dunkel et al. |
| 2006/0116414 A1 | 6/2006 | Dunkel et al. |
| 2008/0015244 A1 | 1/2008 | Dunkel et al. |
| 2009/0036509 A1 | 2/2009 | Gewehr et al. |
| 2017/0044094 A1 | 2/2017 | Himmler et al. |

FOREIGN PATENT DOCUMENTS

| JP | H04316549 A | 11/1992 |
| WO | 03070705 A1 | 8/2003 |
| WO | 2005123689 A1 | 12/2005 |

OTHER PUBLICATIONS

Taccardi, et al., "On the Mechanism of Palladium-Catalyzed Cross-Coupling of Diazonium Salts with Aryltrifluoroborates," Eur. J. Inorg. Chem., (2007), vol. 29: 4645-4652.
Qian, et al., "Palladium-catalyzed ortho-functionalization of azoarenes with aryl acylperoxides," Org. Biomol. Chem., (2014) vol. 12: 5866-5875.
Murahashi, et al, "Reactions of Cyclometalated Palladium Complexes with Organolithium Compounds or Grignard Reagents," J. Org. chem., (1978), vol. 43, No. 21: 4099-4106.
Schabel, et al, "A Mild Chemoselective Ru-Catalyzed Reduction of Alkynes, Ketones, and Nitro Compounds," Organic Letters, (2013), vol. 15, No. 11: 2858-2861.
International Search Report of International Patent Application No. PCT/EP2015/075368 dated Jan. 25, 2016.
Jeong, Nakcheol et al., "A Facile Preparation of the Fluoroaryl Zinc Halides: an Application to the Synthesis of Diflunisal", Bull. Korean Chem. Soc., 2000, pp. 165-166, vol. 21, No. 2.
Miyamura, Sawakon et al., "Rhodium-catalyzed regioselective arylation of phenylazoles and related compounds with arylboron reagents via C-H bond cleavage", Journal of Organometallic Chemistry, 2008, pp. 2438-2442.
Suwa, Kazuya et al., "Syntheses of shuttlecock- and bow-equipped phenylazopyridines and photomodulation of their coordination ability to Zn-porphyrin", Tetrahedron Letters, 2009, pp. 2106-2108, vol. 50.
Cope, Arthur C. et a., "Formation of Covalent Bonds from Platinum or Palladium to Carbon by Direct Substitution", Journal of the American Chemical Society, Jul. 20, 1965, pp. 3272-3273, vol. 87, No. 14.

*Primary Examiner* — Clinton A Brooks
(74) *Attorney, Agent, or Firm* — McBee Moore Woodward & Vanik IP, LLC

(57) ABSTRACT

The present invention relates to a novel method for preparing substituted biphenylamines.

15 Claims, No Drawings

METHOD FOR PRODUCING BIPHENYLAMINES FROM AZOBENZENES BY RUTHENIUM CATALYSIS

CROSS-REFERENCE TO RELATED APPLICATIONS

This application is a National Stage entry of International Application No. PCT/EP2015/075386, filed Nov. 2, 2015, which claims priority to European Patent Application No. 14191403.6, filed Nov. 3, 2014.

BACKGROUND

Field

The present invention relates to a novel method for preparing substituted biphenylamines by ruthenium-catalysed arylation of azobenzenes.

Description of Related Art

Biaryl compounds, especially biphenyl compounds, are of industrial significance as fine chemicals, intermediates for pharmaceuticals, optical brighteners and agrochemicals.

Basic methods for the preparation of biaryl compounds and also the disadvantages associated therewith have already been disclosed and discussed in the European patent application EP 14166058.9.

Disadvantages of these methods include the high production costs. Transition metal-catalysed cross-couplings (for example according to Suzuki) require relatively large amounts of costly palladium catalysts or else (Bull. Korean Chem. Soc. 2000, 21, 165-166) the use of virtually equivalent amounts of zinc which has to be disposed of as waste. Moreover, activation of the zinc requires carcinogenic dibromomethane.

It has already been described as well that azobenzenes halogenated in the ortho position can be arylated with boronic acids catalysed by palladium in a Suzuki-Miyaura reaction (see, for example: K. Suwa et al., Tetrahedron Letters 50 (2009) 2106-8). This method has the disadvantages of using expensive palladium catalysts and the necessity of preparing the halogenated azobenzenes.

It is likewise already known that even non-halogenated azobenzenes can be arylated in the ortho position (S.-I. Murahashi et al., J. Org. Chem. 43 (1978) 4099-4106; N. Taccardi et al., Eur. J. Inorg. Chem. 2007, 4645-52). In this method, however, stoichiometric amounts of palladium complexes are used with azobenzenes (preparation see, for example: A. C. Cope and R. W. Siekman, J. Amer. Chem. Soc. 87 (1965) 3272-3), which renders it uneconomical.

It has also been described already that azobenzenes can be arylated with boronic acids in the presence of rhodium catalysts (S. Miyamura et al., J. Organomet. Chem. 693 (2008) 2438-42). However, rhodium catalysts are exceptionally expensive. In addition, there exists the additional requirement to prepare the boronic acids, typically from the corresponding iodo- or bromoaromatic compounds. Finally, the yields are unsatisfactory (maximum 50%) and only the ortho,ortho' double-arylated compounds are obtained as products.

SUMMARY

The problem addressed by the present invention was thus that of providing a novel method by which biphenylamines can be obtained with a high overall yield and high purity without the use of costly palladium or rhodium catalysts and under industrially preferred reaction conditions.

Accordingly, the present invention provides a method for preparing biphenylamines of the general formula (I)

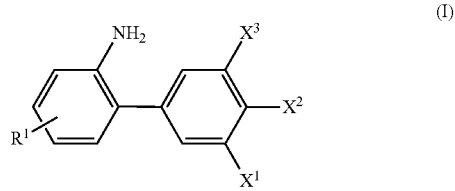

in which
$R^1$ is hydrogen, hydroxyl, fluorine, chlorine, $C_1$-$C_4$-alkyl, $C_1$-$C_4$-alkoxy, $C_1$-$C_4$-alkylthio or $C_1$-$C_4$-haloalkyl,
$X^1$ is hydrogen, alkoxy, alkanoyl, alkyl carboxylate, fluorine or chlorine,
$X^2$ is hydrogen, alkoxy, alkanoyl, alkyl carboxylate, fluorine or chlorine,
$X^3$ is hydrogen, alkoxy, alkanoyl, alkyl carboxylate, fluorine or chlorine,
characterized in that
(1) in a first step
azobenzenes of the formula (II)

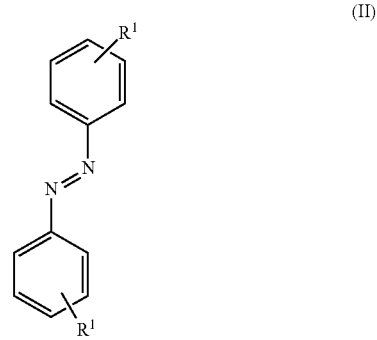

in which
$R^1$ is as defined above,
are reacted with an aromatic compound of the formula (III)

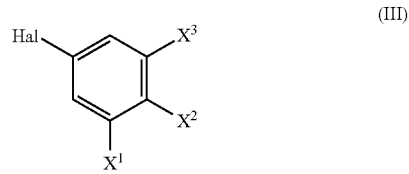

in which
$X^1$, $X^2$ and $X^3$ are as defined above,
and
Hal is iodine, bromine or chlorine
in the presence of a catalyst system consisting of a ruthenium catalyst, an activator, and a base,
and (2) in a second stage the azobenzenes of the formula (IV) thus obtained

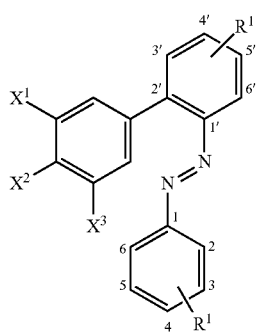

(IV)

in which $R^1$, $X^1$, $X^2$ and $X^3$ are as defined above
and the numbers 1 to 6 and 1' to 6' define the positions of the residue $R^1$ in the compounds specified in Table 1 and also in reference to the positions in formula (IV) in the description,
are hydrogenated to give the biphenylamines of the formula (I).

$C_1$-$C_4$-Alkyl encompasses methyl, ethyl, propyl and isopropyl, butyl, isobutyl and tert-butyl and is more preferably methyl.

$C_1$-$C_4$-Alkoxy encompasses methoxy, ethoxy, propoxy, isopropoxy and butoxy and is more preferably methoxy.

DETAILED DESCRIPTION OF A PREFERRED EMBODIMENT

By means of this reaction sequence, surprisingly, the biphenylamines of the formula (I) may be prepared in good yields without using halogenated azobenzenes, without using expensive palladium or rhodium catalysts, without the necessity of preparing boronic acids and under industrially advantageous reaction conditions.

If azobenzene and bromobenzene are used as starting materials, the method according to the invention can be illustrated by way of example by the following formula scheme:

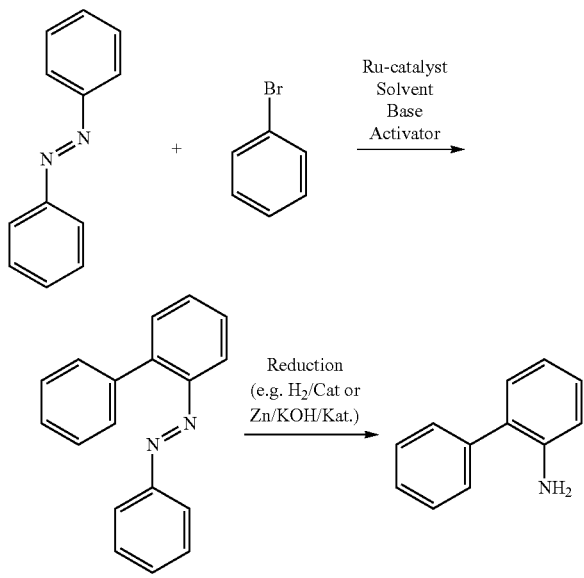

Preference is given to the performance of the method according to the invention using starting materials in which the residues specified are each defined as follows. The preferred, particularly preferred and especially preferred definitions apply to all the compounds in which the respective residues occur:

$R^1$ is preferably hydrogen, fluorine, chlorine, $C_1$-$C_4$-alkyl or $C_1$-$C_4$-alkoxy.

$R^1$ is further preferably fluorine, $C_1$-$C_4$-alkyl and $C_1$-$C_4$-alkoxy, where the substituent is preferably in the 3', 4' or 5' position, further preferably in the 4' or 5' position and more preferably in the 5' position [cf., for example, formula (IV)].

$R^1$ is particularly preferably $C_1$-$C_4$-alkyl and $C_1$-$C_4$-alkoxy, where the substituent is in the 4' or 5' position and particularly preferably in the 5' position [cf., for example, formula (IV)].

In the definitions above for $R^1$, $C_1$-$C_4$-alkyl is preferably selected from the group comprising methyl, ethyl and isopropyl, and $C_1$-$C_4$-alkoxy is preferably selected from the group comprising methoxy and ethoxy.

In an alternative embodiment, $R^1$ is preferably trifluoromethyl, where trifluoromethyl is preferably in the 4' or 5' position, further preferably in the 5' position, of the respective compound.

In a further alternative embodiment, $R^1$ is preferably methoxy or methylthio, preferably in the 4', 5' or 6' position, further preferably in the 5' position, of the respective compound.

$X^1$ is preferably alkoxy, alkanoyl, alkyl carboxylate or chlorine.

$X^1$ is particularly preferably alkoxy, alkanoyl or alkyl carboxylate and especially preferably alkyl carboxylate.

$X^2$ is preferably alkoxy, alkanoyl, alkyl carboxylate or chlorine.

$X^2$ is particularly preferably alkoxy, alkanoyl or alkyl carboxylate and especially preferably alkyl carboxylate.

$X^3$ is preferably alkoxy, alkanoyl, alkyl carboxylate or chlorine.

$X^3$ is particularly preferably alkoxy, alkanoyl or alkyl carboxylate and especially preferably alkyl carboxylate.

In the definitions above, alkyl carboxylate is especially preferably selected from the group comprising methyl, ethyl and isopropyl carboxylate. In the above definitions, alkanoyl is especially preferably selected from the group comprising —COMe, —COEt, —COiPr, —COPr, —CObutyl, —COisobutyl and —COtert-butyl, where Me, Et, and Pr have the customary meanings of methyl, ethyl and propyl.

The azobenzenes of the formula (II) for use as starting materials in the first stage in the performance of the method according to the invention are known or can be obtained by known methods.

The first stage of the method according to the invention is performed in the presence of a ruthenium catalyst. Ruthenium catalysts used are, for example, ruthenium complexes such as [{$RuCl_2$(p-cymene)}$_2$], [{$RuCl_2$(cumene)}$_2$], [{$RuCl_2$(benzene)}$_2$], [{$RuCl_2$($C_6Me_6$)}$_2$], [Cp*Ru(PPh$_3$)$_2$Cl] (Cp*=pentamethylcyclopentadienyl). Preference is given to using [{$RuCl_2$(p-cymene)}$_2$].

The amount of ruthenium catalyst can be varied within wide limits Typically, amounts of 0.1 to 30 mole percent of the relevant complex are used, based on the aromatic compound of the formula (III). Preferably, 1 to 20 mole percent of the relevant complex is used, further preferably 1 to 10 mole percent.

The first stage of the method according to the invention is performed in the presence of an activator.

The activator is preferably an acid, further preferably a carboxylic acid.

By way of example, carboxylic acids include formic acid, acetic acid, propionic acid, pivalic acid, benzoic acid, 2-methylbenzoic acid, 3-methylbenzoic acid, 4-methylbenzoic acid, 2,3-dimethylbenzoic acid, 2,4-dimethylbenzoic acid, 2,5-dimethylbenzoic acid, 2,6-dimethylbenzoic acid, 3,4-dimethylbenzoic acid, 3,5-dimethylbenzoic acid, 2,4,6-trimethylbenzoic acid, 2,3,4-trimethylbenzoic acid, 3,4,5-trimethylbenzoic acid, 2,3,5-trimethylbenzoic acid, 2,3,6-trimethylbenzoic acid, phenylacetic acid, 2-methylphenylacetic acid, 3-methylphenylacetic acid, 4-methylphenylacetic acid, 2,5-dimethylphenylacetic acid, 2,3,6-trimethylphenylacetic acid, 2,3,5,6-tetramethylphenylacetic acid, 2,3,4,6-tetramethylphenylacetic acid, 2-chlorophenylacetic acid, 3-chlorophenylacetic acid, 4-chlorophenylacetic acid and 2,4-dichlorophenylacetic acid.

Preference is given to using 2,4,6-trimethylbenzoic acid (MesCO$_2$H).

The activator is used in amounts of 0.1 to 100 mole percent, based on the aromatic compound of the formula (III). Preferably 1 to 50 mole percent is used, more preferably 10 to 40 mole percent.

The first stage of the method according to the invention is performed in the presence of a base. Organic or inorganic bases are suitable as bases. Examples include ammonia, trimethylamine, triethylamine, tributylamine, diisopropylethylamine, pyrrolidine, piperidine, morpholine, pyridine, 2-picoline, 3-picoline, 4-picoline, 2,3-lutidine, 2,4-lutidine, 2,5-lutidine, 2,6-lutidine, 3,4-lutidine, 3,5-lutidine, 5-ethyl-2-methylpyridine, quinoline, lithium hydroxide, sodium hydroxide, potassium hydroxide, lithium carbonate, sodium carbonate, potassium carbonate, lithium hydrogen carbonate, sodium hydrogen carbonate, potassium hydrogen carbonate, calcium carbonate, magnesium carbonate, lithium acetate, sodium acetate, potassium acetate, lithium pivalate, sodium pivalate and potassium pivalate. Preference is given to using inorganic bases; particularly preferably sodium carbonate, potassium carbonate, sodium hydrogen carbonate, potassium hydrogen carbonate, calcium carbonate, magnesium carbonate, sodium acetate, potassium acetate, sodium pivalate and potassium pivalate.

Particular preference is given to using potassium carbonate.

The first stage of the method according to the invention is performed in solvents or solvent mixtures. Examples include:
ketones such as acetone, diethyl ketone, methyl ethyl ketone and methyl isobutyl ketone;
nitriles such as acetonitrile and butyronitrile;
ethers such as dimethoxyethane (DME), tetrahydrofuran (THF), 2-methyl-THF and 1,4-dioxane; alcohols such as n-propanol, isopropanol, tertiary butanol, isoamyl alcohol or tertiary amyl alcohol;
hydrocarbons and halogenated hydrocarbons such as hexane, heptane, cyclohexane, methylcyclohexane, toluene, ortho-xylene, meta-xylene, para-xylene, mesitylene, chlorobenzene, ortho-dichlorobenzene or nitrobenzene.

The solvent is preferably selected from the group comprising ethers, aromatic hydrocarbons, chlorinated aromatic hydrocarbons and branched alcohols, or mixtures of these solvents. Branched alcohols in the context of the present invention are preferably isopropanol, tertiary butanol, isoamyl alcohol and tertiary amyl alcohol.

The solvent is particularly preferably selected from the group comprising 1,4-dioxane, THF, 2-Me-THF, DME, toluene, ortho-xylene, meta-xylene, para-xylene, mesitylene or tertiary amyl alcohol, or mixtures of these solvents.

Very particular preference is given to the solvents 1,4-dioxane, toluene, ortho-xylene, meta-xylene, para-xylene or mixtures of these solvents.

Solvents which have proven to be unsuitable are methanol, N,N-dialkylalkanamides such as N-methylpyrrolidone, lactones such as γ-valerolactone, water, dimethyl sulphoxide (DMSO) and carboxylic acids such as acetic acid.

The first stage of the method according to the invention is generally performed at temperatures in the range of 20° C. to 220° C., preferably in the range of 50° C. to 180° C., more preferably in the range of 80° C. to 150° C.

In the performance of the first stage of the method according to the invention, generally a substoichiometric amount up to equimolar amounts of haloaromatic compounds of the formula (III) are used per 1 mol of azobenzene of the formula (II). The molar ratio of azobenzene of the formula (II) to haloaromatic compound of the formula (III) is generally 1:0.4 to 1, preferably 1:0.45 to 0.9.

The first stage of the method according to the invention is, unless stated otherwise, generally conducted under atmospheric pressure. However, it is also possible to work under elevated or reduced pressure. The reaction is preferably carried out under atmospheric pressure.

The second stage of the method according to the invention, i.e. the reduction of the azobenzene of the formula (IV) to give a biphenylamine of the formula (I), may be carried out by methods known in principle, for example, by means of zinc and ammonium formate (S. Gowda et al., Tetrahedron Letters 43 (2002) 1329-31); iron and calcium chloride (S. Chandrappa et al., Synlett 2010, 3019-22); ruthenium-catalysed transfer hydrogenation (M. Beller et al., Chem. Eur. J. 2011, 17, 14375-79); ruthenium-catalysed reduction with zinc and KOH (T. Schabel et al., Org. Lett. 15 (2013) 2858-61):

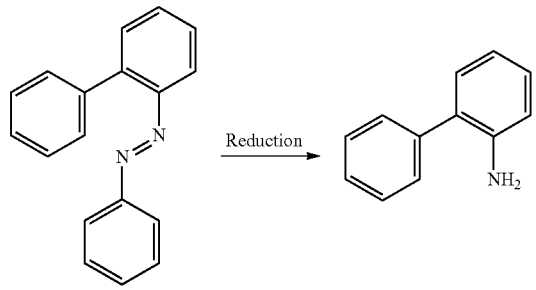 [SMILES: c1ccc(/N=N/c2ccccc2-c2ccccc2)cc1 ; Nc1ccccc1-c1ccccc1]

Ruthenium-catalysed methods are preferably used.

The reduction is particularly preferably carried out in the presence of the ruthenium catalyst which was already used for the first stage of the method according to the invention.

The second stage of the method according to the invention is especially preferably carried out here in such a way that it takes place directly after the first stage of the method according to the invention in a one-pot reaction without isolating the azobenzene of the formula (IV).

In a particularly preferred embodiment, the solvent is selected from the group comprising 1,4-dioxane, toluene, ortho-xylene, meta-xylene, para-xylene or mixtures of these solvents and the activator is 2,4,6-trimethylbenzoic acid, the aromatic compound of the formula (III) is a brominated aromatic compound, the base is potassium carbonate and the catalyst is [{RuCl$_2$(p-cymene)}$_2$].

The biphenylamines of the formula (I) are valuable intermediates for preparation of active fungicidal ingredients (cf. WO 03/070705).

Preferred embodiments of compounds of the formula (IV) in the context of the present invention are (the numbers for $R^1$ each indicate the position and HAL the halogen of the starting compound III):

TABLE 1

| | $R^1$ | $X^1$ | $X^2$ | $X^3$ | HAL |
|---|---|---|---|---|---|
| V1 | Me(3/5') | H | CO$_2$Me | H | Br |
| V8 | Me(3/5') | H | COMe | H | Br |
| V9 | OMe(3/5') | H | COMe | H | Br |
| V10 | Me(2/6') | H | COMe | H | Br |
| V11 | Me(3/5') | H | CO$_2$Et | H | Br |
| V12 | Me(3/5') | H | OMe | H | Br |
| V13 | H | H | H | H | Br |
| V14 | H | H | CO$_2$Me | H | Br |
| V15 | Me(2/6') | H | CO$_2$Me | H | Br |
| V16 | Me(4/4') | H | CO$_2$Me | H | Br |
| V17 | Et(3/5') | H | CO$_2$Me | H | Br |
| V18 | iPr(3/5') | H | CO$_2$Me | H | Br |
| V19 | OMe(3/5') | H | CO$_2$Me | H | Br |
| V20 | H | Cl | Cl | H | Br |
| V21 | Me(3/5') | H | Cl | H | Br |
| V22 | Me(3/5') | Cl | Cl | H | Br |
| V23 | Et(3/5') | H | COMe | H | Br |
| V24 | iPr(3/5') | H | COMe | H | Br |
| V25 | Et(3/5') | H | OMe | H | Br |
| V26 | iPr(3/5') | H | OMe | H | Br |
| V27 | Me(3/5') | H | OEt | H | Br |
| V28 | Me(3/5') | H | OEt | H | Br |
| V29 | Me(3/5') | H | OEt | H | Br |
| V30 | Me(3/5') | H | OiPr | H | Br |
| V31 | Me(3/5') | H | OiPr | H | Br |
| V32 | Me(3/5') | H | OiPr | H | Br |
| V33 | Me(3/5') | H | CO$_2$Et | H | Br |
| V34 | Me(3/5') | H | CO$_2$iPr | H | Br |
| V35 | OMe(3/5') | H | CO$_2$Et | H | Br |
| V36 | OMe(3/5') | H | CO$_2$iPr | H | Br |
| V37 | OMe(3/5') | H | Cl | H | Br |
| V38 | OMe(3/5') | Cl | Cl | H | Br |
| V39 | H | Cl | Cl | Cl | I |
| V40 | H | Cl | H | H | I |
| V41 | H | H | Cl | H | I |
| V42 | H | H | F | H | Br |
| V43 | H | F | F | H | Br |
| V44 | H | F | F | F | Br |
| V45 | H | F | F | F | I |
| V46 | Me(4/4') | H | Cl | H | Br |
| V47 | Me(4/4') | Cl | Cl | H | Br |
| V48 | Me(4/4') | Cl | Cl | Cl | Br |
| V49 | Me(4/4') | H | F | H | Br |
| V50 | Me(4/4') | F | F | H | Br |
| V51 | Me(4/4') | F | F | F | Br |
| V52 | OMe(4/4') | H | Cl | H | Br |
| V53 | OMe(4/4') | Cl | Cl | H | Br |
| V54 | OMe(4/4') | Cl | Cl | Cl | Br |
| V55 | OMe(4/4') | H | F | H | Br |
| V56 | OMe(4/4') | F | F | H | Br |
| V57 | OMe(4/4') | F | F | F | Br |
| V58 | Et(4/4') | Cl | Cl | Cl | Br |
| V59 | OEt(4/4') | Cl | Cl | H | Br |
| V60 | OEt(4/4') | F | F | F | Br |

PREPARATION EXAMPLES

Example 1: Methyl 4'-methyl-2'-[(E)-(3-methylphenyl)diazenyl]biphenyl-4-carboxylate

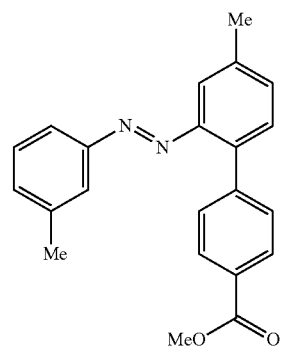

In an oven-dried reaction vessel, a suspension consisting of (E)-bis(3-methylphenyl)diazene (210 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and methyl 4-bromobenzoate (108 mg, 0.5 mmol) was stirred in dry 1,4-dioxane (2.0 ml) at 120° C. for 18 h in a nitrogen atmosphere. The reaction mixture was then diluted at room temperature with dichloromethane (DCM) (75 ml) and filtered through Celite and silica gel, and the filtrate was concentrated. The crude product thus obtained was purified by chromatography on silica gel (n-hexane/DCM: 7/3). 150 mg of methyl 4'-methyl-2'-[(E)-(3-methylphenyl)diazenyl]biphenyl-4-carboxylate were obtained as an orange solid (87% of theory).

M.p.=136-137° C. $^1$H-NMR (CDCl$_3$, 300 MHz): δ=8.10 (d, J=8.0 Hz, 2H), 7.64 (s, 1H), 7.60-7.53 (m, 4H), 7.49 (d, J=7.8 Hz, 1H), 7.40-7.32 (m, 2H), 7.30-7.24 (m, 1H), 3.96 (s, 3H), 2.48 (s, 3H), 2.42 (s, 3H). $^{13}$C-NMR (CDCl$_3$, 126 MHz): δ=167.0 (Cq), 152.7 (Cq), 149.3 (Cq), 143.6 (Cq), 138.8 (Cq), 138.7 (Cq), 137.1 (Cq), 131.7 (CH), 131.5 (CH), 130.7 (CH), 130.4 (CH), 128.8 (CH), 128.7 (CH), 128.5 (Cq), 124.2 (CH), 119.8 (CH), 116.1 (CH), 52.1 (CH$_3$), 21.4 (CH$_3$), 21.3 (CH$_3$). IR (neat): 3030, 2951, 2914, 2850, 1721, 1606, 1438, 1279, 1106, 829, 790, 704, 533, 475, 436 cm-1. MS (EI) m/z (relative intensity): 344 ([M+] 60), 329 (80), 285 (38), 225 (43), 165 (87), 91 (100), 65 (25), 43 (22). HR-MS (EI) m/z calculated for C$_{22}$H$_{20}$N$_2$O$_2$ [M+] 344.1525, found 344.1511.

Example 2: Methyl 4'-methyl-2'-[(E)-(3-methylphenyl)diazenyl]biphenyl-4-carboxylate The experiment was carried out as described for Example 1, with the difference that toluene was used as solvent in place of 1,4-dioxane. The yield was 83% of theory.

Example 3: Methyl 4'-methyl-2'-[(E)-(3-methylphenyl)diazenyl]biphenyl-4-carboxylate The experiment was carried out as described for Example 1, with the difference that ortho-xylene was used as solvent in place of 1,4-dioxane. The yield was 84% of theory.

Example 4: Methyl 4'-methyl-2'-[(E)-(3-methylphenyl)diazenyl]biphenyl-4-carboxylate The experiment was carried out as described for Example 1, with the difference that tertiary amyl alcohol was used as solvent in place of 1,4-dioxane. The yield was 75% of theory.

Example 5: Methyl 4'-methyl-2'-[(E)-(3-methylphenyl)diazenyl]biphenyl-4-carboxylate The experiment was carried out as described for Example 1, with the difference that sodium carbonate was used as base in place of potassium carbonate. The yield was 75% of theory.

Example 6: Methyl 4'-methyl-2'-[(E)-(3-methylphenyl)diazenyl]biphenyl-4-carboxylate The experiment was carried out as described for Example 1, with the difference that potassium acetate was used as additive in place of $MesCO_2H$. The yield was 79% of theory.

Example 7: Methyl 4'-methyl-2'-[(E)-(3-methylphenyl)diazenyl]biphenyl-4-carboxylate The experiment was carried out as described for Example 1, with the difference that pivalic acid was used as additive in place of $MesCO_2H$. The yield was 76% of theory.

Example 8: 1-{4'-Methyl-2'-[(E)-(3-methylphenyl)diazenyl]biphenyl-4-yl}ethanone

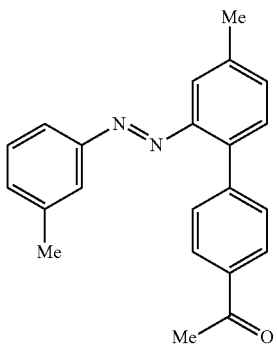

In an oven-dried reaction vessel, a suspension consisting of (E)-1,2-di-m-tolyldiazene (210 mg, 1.0 mmol), [{RuCl$_2$(p-cymene)}$_2$] (15.3 mg, 5.0 mol %), $MesCO_2H$ (24.6 mg, 30 mol %), $K_2CO_3$ (138 mg, 1.0 mmol) and 4-bromoacetophenone (99.5 mg, 0.5 mmol) was stirred in dry 1,4-dioxane (2.0 ml) at 120° C. for 18 h in a nitrogen atmosphere. The reaction mixture was then diluted at room temperature with dichloromethane (DCM) (75 ml) and filtered through Celite and silica gel, and the filtrate was concentrated. The crude product thus obtained was purified by chromatography on silica gel (n-hexane/DCM: 7/3). 106 mg of 1-{4'-methyl-2'-[(E)-(3-methylphenyl)diazenyl]biphenyl-4-yl}ethanone were obtained (65% of theory).

M.p.=123-124° C. $^1$H-NMR (CDCl$_3$, 300 MHz): δ=8.00 (d, J=8.6 Hz, 2H), 7.64-7.50 (m, 5H), 7.46 (d, J=7.8 Hz, 1H), 7.39-7.29 (m, 2H), 7.28-7.21 (m, 1H), 2.64 (s, 3H), 2.47 (s, 3H), 2.40 (s, 3H). $^{13}$C-NMR (CDCl$_3$, 126 MHz): δ=198.1 ($C_q$), 152.9 ($C_q$), 149.6 ($C_q$), 144.0 ($C_q$), 139.0 ($C_q$), 138.9 ($C_q$), 137.2 ($C_q$), 135.6 ($C_q$), 131.9 (CH), 131.7 (CH), 131.0 (CH), 130.5 (CH), 129.0 (CH), 127.6 (CH), 124.4 (CH), 119.9 (CH), 116.3 (CH), 26.5 (CH$_3$), 21.2 (CH$_3$), 21.1 (CH$_3$). IR (neat): 2914, 2856, 2723, 1679, 1600, 1266, 819, 797, 688, 599 cm$^{-1}$. MS (EI) m/z (relative intensity): 328 ([M$^+$] 100), 285 (44), 209 (25), 165 (41), 91 (83), 65 (19), 65 (20), 43 (76). HR-MS (EI) m/z calculated for $C_{22}H_{20}N_2O$ [M$^+$] 328.1576, found 328.1572.

Example 9: 1-{4'-Methoxy-2'-[(E)-(3-methoxyphenyl)diazenyl]biphenyl-4-yl}ethanone

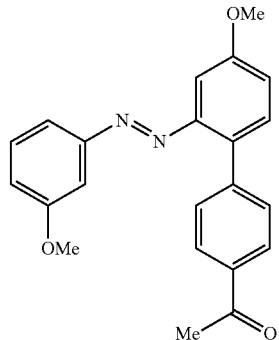

In an oven-dried reaction vessel, a suspension consisting of (E)-bis(3-methoxyphenyl)diazene (242 mg, 1.0 mmol), [{RuCl$_2$(p-cymene)}$_2$] (15.3 mg, 5.0 mol %), $MesCO_2H$ (24.6 mg, 30 mol %), $K_2CO_3$ (138 mg, 1.0 mmol) and 4-bromoacetophenone (99.5 mg, 0.5 mmol) was stirred in dry 1,4-dioxane (2.0 ml) at 120° C. for 18 h in a nitrogen atmosphere. The reaction mixture was then diluted at room temperature with dichloromethane (DCM) (75 ml) and filtered through Celite and silica gel, and the filtrate was concentrated. The crude product thus obtained was purified by chromatography on silica gel (n-hexane/DCM: 7/3). 96 mg of 1-{4'-methoxy-2'-[(E)-(3-methoxyphenyl)diazenyl] biphenyl-4-yl}ethanone were obtained (53% of theory).

M.p.=155-156° C. $^1$H-NMR (CDCl$_3$, 300 MHz): δ=7.98 (d, J=8.5 Hz, 2H), 7.61-7.22 (m, 7H), 7.13 (dd, J=8.6, 2.7 Hz, 1H), 7.00 (ddd, J=8.0, 2.7, 1.2 Hz, 1H), 3.91 (s, 3H), 3.78 (s, 3H), 2.63 (s, 3H). $^{13}$C-NMR (CDCl$_3$, 126 MHz): δ=198.1 ($C_q$), 160.4 ($C_q$), 160.2 ($C_q$), 154.0 ($C_q$), 150.2 ($C_q$), 143.8 ($C_q$), 135.4 ($C_q$), 133.4 ($C_q$), 131.6 (CH), 131.1 (CH), 129.9 (CH), 127.6 (CH), 118.5 (CH), 118.0 (CH), 117.4 (CH), 106.4 (CH), 99.4 (CH), 55.6 (CH$_3$), 55.3 (CH$_3$), 26.6 (CH$_3$). IR (neat): 3068, 3005, 2961, 2940, 2915, 2834, 1673, 1604, 1513, 1269, 1132, 1040, 887, 819, 782, 634 cm$^{-1}$. MS (EI) m/z (relative intensity): 360 ([M$^+$] 100), 317 (57), 139 (38), 107 (53), 92 (24), 77 (30), 43 (54). HR-MS (EI) m/z calculated for $C_{22}H_{20}N_2O_3$ [M$^+$] 360.1474, found 360.1466.

Example 10: 1-{3'-Methyl-2'-[(E)-(2-methylphenyl)diazenyl]biphenyl-4-yl}ethanone

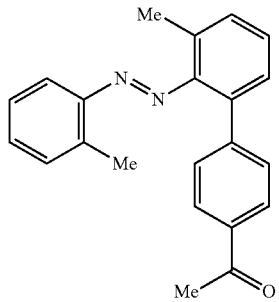

In an oven-dried reaction vessel, a suspension consisting of (E)-bis(2-methylphenyl)diazene (210 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and 4-bromoacetophenone (99.5 mg, 0.5 mmol) was stirred in dry 1,4-dioxane (2.0 ml) at 120° C. for 18 h in a nitrogen atmosphere. The reaction mixture was then diluted at room temperature with dichloromethane (DCM) (75 ml) and filtered through Celite and silica gel, and the filtrate was concentrated. The crude product thus obtained was purified by chromatography on silica gel (n-hexane/DCM: 7/3). 87 mg of 1-{3'-methyl-2'-[(E)-(2-methylphenyl)diazenyl]biphenyl-4-yl}ethanone were obtained (53% of theory).

M.p.=125-126° C. (CDCl$_3$, 300 MHz): δ=7.89 (d, J=8.6 Hz, 2H), 7.38-7.20 (m, 9H), 2.59 (s, 3H), 2.46 (s, 3H), 2.27 (s, 3H). $^{13}$C-NMR (CDCl$_3$, 126 MHz): δ=198.0 (C$_q$), 151.0 (C$_q$), 150.8 (C$_q$), 145.7 (C$_q$), 138.5 (C$_q$), 135.2 (C$_q$), 134.7 (C$_q$), 131.5 (CH), 131.4 (CH), 131.3 (CH), 130.9 (C$_q$), 130.4 (CH), 128.9 (CH), 128.2 (CH), 128.0 (CH), 126.4 (CH), 115.0 (CH), 26.5 (CH$_3$), 19.1 (CH$_3$), 17.0 (CH$_3$). IR (neat): 3054, 2961, 2923, 1679, 1603, 1356, 1264, 955, 766, 600 cm$^{-1}$. MS (EI) m/z (relative intensity): 328 ([M$^+$] 100), 285 (32), 209 (25), 165 (45), 91 (98), 65 (27), 43 (90). HR-MS (EI) m/z calculated for C$_{22}$H$_{20}$N$_2$O [M$^+$] 328.1576, found 328.1569.

Example 11: Ethyl 4'-methyl-2'-[(E)-(3-methylphenyl)diazenyl]biphenyl-4-carboxylate

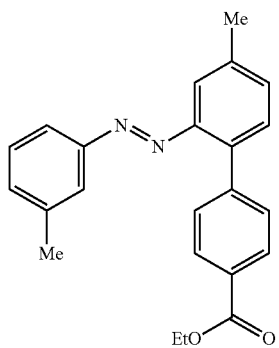

In an oven-dried reaction vessel, a suspension consisting of (E)-bis(3-methylphenyl)diazene (210 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and ethyl 4-bromobenzoate (107 mg, 0.5 mmol) was stirred in dry 1,4-dioxane (2.0 ml) at 120° C. for 18 h in a nitrogen atmosphere. The reaction mixture was then diluted at room temperature with dichloromethane (DCM) (75 ml) and filtered through Celite and silica gel, and the filtrate was concentrated. The crude product thus obtained was purified by chromatography on silica gel (n-hexane/DCM: 7/3). 113 mg of ethyl 4'-methyl-2'-[(E)-(3-methylphenyl)diazenyl]biphenyl-4-carboxylate were obtained (63% of theory).

M.p.=94-95° C. $^1$H-NMR (CDCl$_3$, 300 MHz): δ=8.09 (d, J=8.5 Hz, 2H), 7.63-7.60 (m, 1H), 7.58-7.50 (m, 4H), 7.47 (d, J=7.9 Hz, 1H), 7.39-7.30 (m, 2H), 7.28-7.22 (m, 1H), 4.41 (q, J=7.1 Hz, 2H), 2.47 (s, 3H), 2.41 (s, 3H), 1.41 (t, J=7.1 Hz, 3H). $^{13}$C-NMR (CDCl$_3$, 126 MHz): δ=166.8 (C$_q$), 153.0 (C$_q$), 149.6 (C$_q$), 143.7 (C$_q$), 139.0 (C$_q$), 138.9 (C$_q$), 137.4 (C$_q$), 131.9 (CH), 131.7 (CH), 130.8 (CH), 130.6 (CH), 129.0 (C$_q$), 128.9 (CH), 128.8 (CH), 124.4 (CH), 119.9 (CH), 116.3 (CH), 60.9 (CH$_2$), 21.3 (CH$_3$), 21.1 (CH$_3$), 14.3 (CH$_3$). IR (neat): 2979, 2921, 2867, 1713, 1607, 1268, 1180, 1100, 775, 688 cm$^{-1}$. MS (EI) m/z (relative intensity): 358 ([M$^+$]47), 329 (100), 285 (37), 239 (19), 211 (17), 165 (60), 91 (80), 65 (14). HR-MS (EI) m/z calculated for C$_{23}$H$_{22}$N$_2$O$_2$ [M$^+$] 358.1681, found 358.1669.

Example 12: (E)-1-(4'-Methoxy-4-methylbiphenyl-2-yl)-2-(3-methylphenyl)diazene

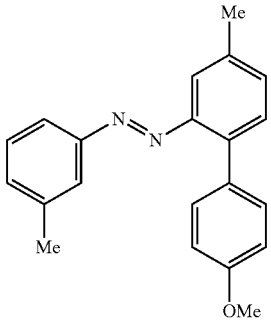 [SMILES: COc1ccc(-c2ccc(C)cc2/N=N/c2cccc(C)c2)cc1]

In an oven-dried reaction vessel, a suspension consisting of (E)-bis(3-methylphenyl)diazene (210 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and 4-bromoanisole (93.5 mg, 0.5 mmol) was stirred in dry 1,4-dioxane (2.0 ml) at 120° C. for 18 h in a nitrogen atmosphere. The reaction mixture was then diluted at room temperature with dichloromethane (DCM) (75 ml) and filtered through Celite and silica gel, and the filtrate was concentrated. The crude product thus obtained was purified by chromatography on silica gel (n-hexane/DCM: 7/3). 106 mg of (E)-1-(4'-methoxy-4-methylbiphenyl-2-yl)-2-(3-methylphenyl)diazene were obtained (67% of theory).

M.p.=121-122° C. $^1$H-NMR (CDCl$_3$, 300 MHz): δ=7.69-7.59 (m, 2H), 7.55-7.52 (m, 1H), 7.47 (d, J=7.8 Hz, 1H), 7.43-7.31 (m, 4H), 7.29-7.23 (m, 1H), 6.97 (d, J=8.9 Hz, 2H), 3.87 (s, 3H), 2.46 (s, 3H), 2.43 (s, 3H). $^{13}$C-NMR (CDCl$_3$, 126 MHz): δ=158.8 (C$_q$), 152.9 (C$_q$), 149.4 (C$_q$), 138.8 (C$_q$), 137.7 (C$_q$), 137.3 (C$_q$), 131.9 (CH), 131.5 (CH), 131.4 (CH), 131.1 (C$_q$), 130.4 (CH), 128.7 (CH), 124.0 (CH), 120.0 (CH), 116.0 (CH), 113.0 (CH), 55.3 (CH$_3$), 21.4 (CH$_3$), 21.2 (CH$_3$). IR (neat): 2962, 2914, 2856, 1606, 1518, 1249, 1177, 1016, 816, 791, 689, 538 cm$^{-1}$. MS (EI) m/z (relative intensity): 316 ([M$^+$]100), 301 (40), 197 (67), 182

(65), 153 (42), 91 (78), 65 (30). HR-MS (EI) m/z calculated for $C_{21}H_{20}N_2O$ [M$^+$] 316.1576, found 316.1577.

Example 13: (E)-1-(Biphenyl-2-yl)-2-phenyldiazene

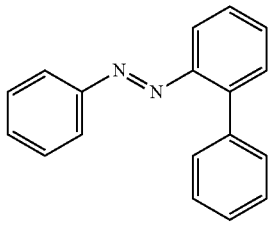 [SMILES: c1ccc(/N=N/c2ccccc2-c2ccccc2)cc1]

In an oven-dried reaction vessel, a suspension consisting of (E)-1,2-diphenyldiazene (182 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and bromobenzene (79 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/EtOAc/NEt$_3$: 88/6/6). (E)-1-(Biphenyl-2-yl)-2-phenyldiazene (68 mg, 53%) was obtained as an orange viscous oil.

$^1$H-NMR (CDCl$_3$, 300 MHz): δ=7.81-7.75 (m, 2H), 7.62-7.35 (m, 12H). $^{13}$C-NMR (CDCl$_3$, 126 MHz): δ=152.9 (C$_q$), 149.8 (C$_q$), 141.2 (C$_q$), 138.9 (C$_q$), 131.1 (CH), 131.0 (CH), 130.9 (CH), 130.8 (CH), 129.1 (CH), 128.1 (CH), 127.7 (CH), 127.3 (CH), 123.3 (CH), 116.0 (CH). IR (neat): 3058, 3030, 1470, 1149, 1008, 770, 730, 685, 535, 497 cm$^{-1}$. MS (EI) m/z (relative intensity): 258 ([M+] 42), 152 (82), 84 (100), 77 (70). HR-MS (EI) m/z calculated for $C_{18}H_{14}N_2$ [M$^+$] 258.1157, found 258.1152.

Example 14: Methyl 2'-[(E)-phenyldiazenyl]biphenyl-4-carboxylate

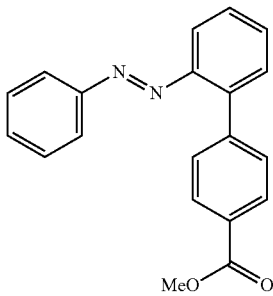 [SMILES: COC(=O)c1ccc(-c2ccccc2/N=N/c2ccccc2)cc1]

In an oven-dried reaction vessel, a suspension consisting of (E)-1,2-diphenyldiazene (182 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and methyl 4-bromobenzoate (108 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/CH$_2$Cl$_2$: 7/3). Methyl 2'-[(E)-phenyldiazenyl]biphenyl-4-carboxylate (93 mg, 59%) was obtained as an orange solid.

M.p.=128-129° C. $^1$H-NMR (CDCl$_3$, 500 MHz): δ=8.09 (d, J=8.6 Hz, 2H), 7.80-7.72 (m, 3H), 7.57-7.52 (m, 4H), 7.51-7.42 (m, 4H), 3.94 (s, 3H). $^{13}$C-NMR (CDCl$_3$, 126 MHz): δ=167.2 (C$_q$), 152.7 (C$_q$), 149.6 (C$_q$), 143.7 (C$_q$), 140.2 (C$_q$), 131.1 (CH), 130.9 (CH), 130.9 (CH), 130.7 (CH), 129.1 (CH), 128.9 (CH), 128.8 (C$_q$), 128.7 (CH), 123.3 (CH), 116.0 (CH), 52.1 (CH$_3$). IR (neat): 3071, 2947, 2920, 2848, 1721, 1437, 1273, 1103, 774, 736, 686, 541 cm$^{-1}$. MS (EI) m/z (relative intensity): 316 ([M$^+$]58), 301 (100), 257 (40), 211 (44), 152 (91), 77 (94). HR-MS (EI) m/z calculated for $C_{20}K_{16}N_2O_2$ [M$^+$]316.1212, found 316.1205.

Example 15: Methyl 3'-methyl-2'-[(E)-(2-methylphenyl)diazenyl]biphenyl-4-carboxylate

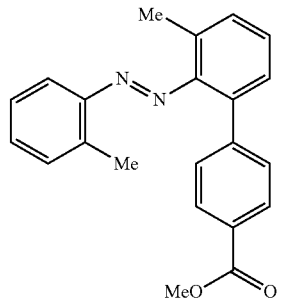

In an oven-dried reaction vessel, a suspension consisting of (E)-1,2-di-o-tolyldiazene (210 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and methyl 4-bromobenzoate (108 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/CH$_2$Cl$_2$: 7/3). Methyl 3'-methyl-2'-[(E)-(2-methylphenyl)diazenyl]biphenyl-4-carboxylate (103 mg, 60%) was obtained as an orange solid.

M.p.=123-124° C. $^1$H-NMR (CDCl$_3$, 500 MHz): δ=7.97 (d, J=8.1 Hz, 2H), 7.38-7.26 (m, 9H), 3.92 (s, 3H), 2.47 (s, 3H), 2.28 (s, 3H). $^{13}$C-NMR (CDCl$_3$, 126 MHz): δ=167.1 (C$_q$), 150.9 (C$_q$), 150.7 (C$_q$), 145.4 (C$_q$), 138.5 (C$_q$), 134.7 (C$_q$), 131.3 (CH), 131.2 (CH), 131.1 (CH), 130.8 (C$_q$), 130.1 (CH), 129.1 (CH), 128.9 (CH), 128.1 (CH), 128.0 (C$_q$), 126.3 (CH), 115.0 (CH), 52.0 (CH$_3$), 19.2 (CH$_3$), 17.1 (CH$_3$). IR (neat): 3059, 2951, 2923, 2844, 1719, 1608, 1398, 1272, 1179, 1101, 856, 766, 739, 712 cm$^{-1}$. MS (EI) m/z (relative intensity): 344 ([M$^+$] 60), 329 (93), 285 (30), 225 (50), 165 (99), 91 (100), 65 (34). HR- MS (EI) m/z calculated for $C_{22}H_{20}N_2O_2$ [M$^+$] 344.1525, found 344.1526.

Example 16: Methyl 5'-methyl-2'-[(E)-(4-methylphenyl)diazenyl]biphenyl-4-carboxylate

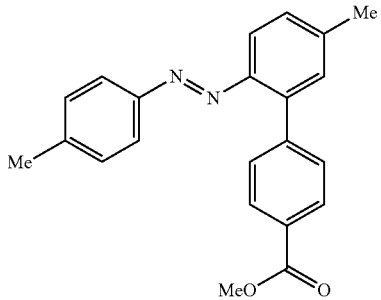 [SMILES: COC(=O)c1ccc(-c2cc(C)ccc2/N=N/c2ccc(C)cc2)cc1]

In an oven-dried reaction vessel, a suspension consisting of (E)-1,2-di-p-tolyldiazene (210 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and methyl 4-bromobenzoate (108 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/CH$_2$Cl$_2$: 7/3). Methyl 5'-methyl-2'-[(E)-(4-methylphenyl)diazenyl]biphenyl-4-carboxylate (112 mg, 65%) was obtained as an orange solid.

M.p.=138-139° C. $^1$H-NMR (CDCl$_3$, 500 MHz): δ=8.08 (d, J=8.6 Hz, 2H), 7.71 (d, J=8.2 Hz, 1H), 7.64 (d, J=8.2 Hz, 2H), 7.54 (d, J=8.6 Hz, 2H), 7.37-7.35 (m, 1H), 7.27 (ddq, J=8.2, 2.0, 0.6 Hz, 1H), 7.25-7.21 (m, 2H), 3.94 (s, 3H), 2.46 (s, 3H), 2.39 (s, 3H). $^{13}$C-NMR (CDCl$_3$, 126 MHz): δ=167.2 (C$_q$), 151.0 (C$_q$), 147.6 (C$_q$), 143.9 (C$_q$), 141.4 (C$_q$), 141.1 (C$_q$), 140.0 (C$_q$), 131.1 (CH), 130.8 (CH), 129.7 (CH), 129.5 (CH), 128.7 (CH), 128.6 (C$_q$), 123.1 (CH), 115.8 (CH), 52.1 (CH$_3$), 21.5 (CH$_3$). IR (neat): 3029, 2948, 2921, 2844, 1721, 1599, 1437, 1274, 1149, 1112, 824, 702, 565, 385 cm$^{-1}$. MS (EI) m/z (relative intensity): 344 ([M$^+$] 66), 329 (73), 285 (29), 225 (47), 165 (86), 91 (100), 65 (25). HR-MS (ESI) m/z calculated for C$_{22}$H$_{21}$N$_2$O$_2$ [M+H$^+$] 345.1603, found 345.1599.

Example 17: Methyl 4'-ethyl-2'-[(E)-(3-ethylphenyl)diazenyl]biphenyl-4-carboxylate

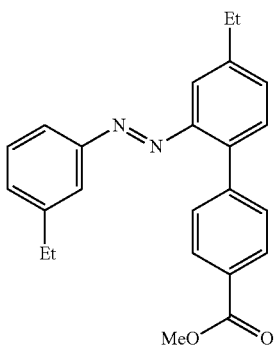 [SMILES: CCc1cccc(/N=N/c2cc(CC)ccc2-c2ccc(C(=O)OC)cc2)c1]

In an oven-dried reaction vessel, a suspension consisting of (E)-1,2-bis(3-ethylphenyl)diazene (238 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and methyl 4-bromobenzoate (108 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/CH$_2$Cl$_2$: 7/3). Methyl 4'-ethyl-2'-[(E)-(3-ethylphenyl)diazenyl]biphenyl-4-carboxylate (155 mg, 83%) was obtained as an orange solid. M.p.=81-82° C. $^1$H-NMR (CDCl$_3$, 500 MHz): δ=8.07 (d, J=8.6 Hz, 2H), 7.68-7.65 (m, 1H), 7.61-7.59 (m, 1H), 7.57-7.52 (m, 3H), 7.50 (dd, J=7.9, 0.5 Hz, 1H), 7.39 (dd, J=7.9, 1.8 Hz, 1H), 7.35 (t, J=7.7 Hz, 1H), 7.29-7.26 (m, 1H), 3.94 (s, 3H), 2.77 (q, J=7.6 Hz, 2H), 2.71 (q, J=7.6 Hz, 2H), 1.32 (t, J=7.6 Hz, 3H), 1.26 (t, J=7.6 Hz, 3H). $^{13}$C-NMR (CDCl$_3$, 126 MHz): δ=167.2 (C$_q$), 153.0 (C$_q$), 149.6 (C$_q$), 145.3 (C$_q$), 145.2 (C$_q$), 143.8 (C$_q$), 137.5 (C$_q$), 130.9 (CH), 130.7 (CH), 130.6 (CH), 130.5 (CH), 129.0 (CH), 128.8 (CH), 128.6 (C$_q$), 123.4 (CH), 119.8 (CH), 115.0 (CH), 52.1 (CH$_3$), 28.7 (CH$_2$), 28.7 (CH$_2$), 15.4 (CH$_3$), 15.3 (CH$_3$). IR (neat): 2962, 2930, 2871, 1717, 1606, 1439, 1273, 1181, 1102, 691 cm$^{-1}$. MS (EI) m/z (relative intensity): 372 ([M$^+$] 89), 357 (100), 313 (45), 239 (61), 180 (35), 165 (75), 105 (91), 77 (32). HR-MS (ESI) m/z calculated for C$_{24}$H$_{25}$N$_2$O$_2$ [M+H$^+$] 373.1916, found 373.1915.

Example 18: Methyl 4'-isopropyl-2'-[(E)-(3-isopropylphenyl)diazenyl]biphenyl-4-carboxylate

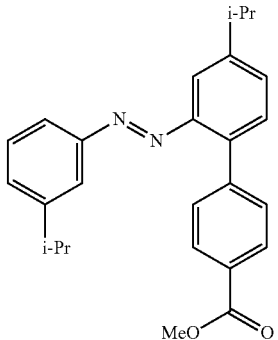

In an oven-dried reaction vessel, a suspension consisting of (E)-1,2-bis(3-isopropylphenyl)diazene (266 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and methyl 4-bromobenzoate (108 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/CH$_2$Cl$_2$: 4/6). Methyl 4'-isopropyl-2'-[(E)-(3-isopropylphenyl)diazenyl]biphenyl-4-carboxylate (160 mg, 80%) was obtained as an orange solid. M.p.=92-93° C. $^1$H-NMR (CDCl$_3$, 500 MHz): δ=8.07 (d, J=8.5 Hz, 2H), 7.71 (t, J=1.8 Hz, 1H), 7.63 (d, J=1.9 Hz, 1H), 7.56-7.50 (m, 4H), 7.43 (dd, J=8.0, 1.9 Hz, 1H), 7.35 (t, J=7.7 Hz, 1H), 7.32-7.29 (m, 1H), 3.93 (s, 3H), 3.04 (sept, J=6.9 Hz, 1H), 2.97 (sep, J=6.9 Hz, 1H), 1.33 (d, J=6.9 Hz, 6H), 1.27 (d, J=6.9 Hz, 6H). $^{13}$C-NMR (CDCl$_3$, 126 MHz): δ=167.2 (C$_q$), 153.0 (C$_q$), 150.0 (C$_q$), 149.9 (C$_q$), 149.5 (C$_q$), 143.8 (C$_q$), 137.7 (C$_q$), 130.9 (CH), 130.6 (CH), 129.4 (CH), 129.1 (CH), 129.0 (CH), 128.8 (CH), 128.6 (C$_q$), 122.4 (CH), 119.6 (CH), 113.7 (CH), 52.1 (CH$_3$), 34.1 (CH), 34.0 (CH), 23.9 (CH$_3$), 23.8 (CH$_3$). IR (neat): 2959, 2889, 2868, 1718, 1607, 1439, 1273, 1113, 858, 835, 797, 694 cm$^{-1}$. MS (EI) m/z (relative intensity): 400 ([M$^+$] 96), 385 (100), 341 (41), 253 (45), 211 (47), 179 (43), 119 (78), 91 (42). HR-MS (EI) m/z calculated for C$_{26}$H$_{28}$N$_2$O$_2$ [M$^+$] 400.2151, found 400.2138.

Example 19: Methyl 4'-methoxy-2'-[(E)-(3-methoxyphenyl)diazenyl]biphenyl-4-carboxylate

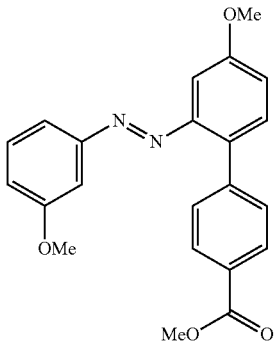 [SMILES: COC(=O)c1ccc(-c2ccc(OC)cc2/N=N/c2cccc(OC)c2)cc1]

In an oven-dried reaction vessel, a suspension consisting of (E)-1,2-bis(3-methoxyphenyl)diazene (242 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and methyl 4-bromobenzoate (108 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/CH$_2$Cl$_2$: 4/6). Methyl 4'-methoxy-2'-[(E)-(3-methoxyphenyl)diazenyl]biphenyl-4-carboxylate (139 mg, 74%) was obtained as an orange solid. M.p.=145-146° C. $^1$H-NMR (CDCl$_3$, 500 MHz): δ=8.06 (d, J=8.6 Hz, 2H), 7.53-7.48 (m, 3H), 7.44 (ddd, J=7.8, 1.7, 1.0 Hz, 1H), 7.37 (d, J=8.1 Hz, 1H), 7.35-7.33 (m, 1H), 7.27 (dd, J=2.6, 1.7 Hz, 1H), 7.13 (dd, J=8.5, 2.7 Hz, 1H), 7.02-6.98 (m, 1H), 3.93 (s, 3H), 3.91 (s, 3H), 3.78 (s, 3H). $^{13}$C-NMR (CDCl$_3$, 126 MHz): δ=167.1 (C$_q$), 160.3 (C$_q$), 160.0 (C$_q$), 153.9 (C$_q$), 150.0 (C$_q$), 143.5 (C$_q$), 133.5 (C$_q$), 131.6 (CH), 130.9 (CH), 129.8 (CH), 128.7 (CH), 128.4 (C$_q$), 118.4 (CH), 118.0 (CH), 117.4 (CH), 106.2 (CH), 99.3 (CH), 55.6 (CH$_3$), 55.3 (CH$_3$), 52.1 (CH$_3$). IR (neat): 2950, 2902, 2834, 1719, 1597, 1519, 1481, 1433, 1270, 1132, 1103, 1039, 887, 782, 683 cm$^{-1}$. MS (EI) m/z (relative intensity): 376 ([M$^+$] 64), 361 (100), 317 (53), 241 (38), 182 (35), 139 (54), 107 (65), 77 (38). HR-MS (ESI) m/z calculated for C$_{22}$H$_{21}$N$_2$O$_4$ [M+H$^+$] 377.1501, found 377.1491.

Example 20: (E)-1-(3',4'-Dichlorobiphenyl-2-yl)-2-phenyldiazene

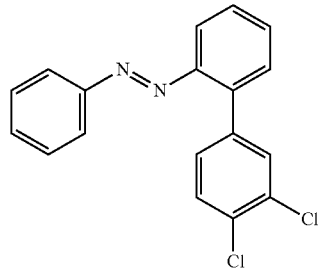 [SMILES: Clc1ccc(-c2ccccc2/N=N/c2ccccc2)cc1Cl]

In an oven-dried reaction vessel, a suspension consisting of (E)-1,2-diphenyldiazene (182 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and 4-bromo-1,2-dichlorobenzene (113 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/EtOAc/NEt$_3$: 88/6/6). (E)-1-(3',4'-Dichlorobiphenyl-2-yl)-2-phenyldiazene (79 mg, 48%) was obtained as an orange solid.
M.p.=128-129° C. $^1$H-NMR (CDCl$_3$, 600 MHz): δ=7.81-7.77 (m, 3H), 7.62 (d, J=2.1 Hz, 1H), 7.54-7.52 (m, 2H), 7.51-7.45 (m, 5H), 7.29 (dd, J=8.3, 2.1 Hz, 1H). $^{13}$C-NMR (CDCl$_3$, 126 MHz): δ=152.8 (C$_q$), 149.4 (C$_q$), 139.0 (C$_q$), 138.9 (C$_q$), 132.5 (CH), 131.8 (C$_q$), 131.6 (C$_q$), 131.3 (CH), 131.1 (CH), 130.5 (CH), 130.3 (CH), 129.5 (CH), 129.2 (CH), 128.9 (CH), 123.3 (CH), 116.1 (CH). IR (neat): 3092, 3055, 1459, 1374, 1137, 1023, 817, 772, 755, 740, 684, 551 cm$^{-1}$. MS (EI) m/z (relative intensity): 326 ([M$^+$] 35), 221 (26), 186 (72), 151 (26), 105 (28), 77 (100), 51 (30). HR-MS (ESI) m/z calculated for C$_{18}$H$_{13}$Cl$_2$N$_2$ [M+H$^+$] 327.0456, found 327.0451.

Example 21: (E)-1-(4'-Chloro-4-methylbiphenyl-2-yl)-2-(3-methylphenyl)diazene

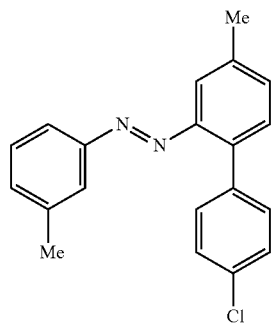 [SMILES: Cc1cccc(/N=N/c2cc(C)ccc2-c2ccc(Cl)cc2)c1]

In an oven-dried reaction vessel, a suspension consisting of (E)-1,2-di-m-tolyldiazene (210 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and 1-bromo-4-chlorobenzene (96 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/EtOAc/NEt$_3$: 88/6/6). (E)-1-(4'-Chloro-4-methylbiphenyl-2-yl)-2-(3-methylphenyl)diazene (93 mg, 58%) was obtained as an orange solid.

M.p.=120-121° C. $^1$H-NMR (CDCl$_3$, 500 MHz): δ=7.73-7.69 (m, 1H), 7.60 (s, 1H), 7.58-7.52 (m, 2H), 7.42 (d, J=7.9 Hz, 1H), 7.38-7.36 (m, 3H), 7.36-7.32 (m, 2H), 7.29-7.25 (m, 1H), 2.45 (s, 3H), 2.41 (s, 3H). $^{13}$C-NMR (CDCl$_3$, 126 MHz): δ=152.9 (C$_q$), 149.5 (C$_q$), 139.0 (C$_q$), 138.5 (C$_q$), 137.3 (C$_q$), 137.1 (C$_q$), 133.2 (C$_q$), 132.1 (CH), 131.8 (CH), 131.7 (CH), 130.4 (CH), 128.9 (CH), 127.7 (CH), 124.2 (CH), 120.0 (CH), 116.2 (CH), 21.4 (CH$_3$), 21.2 (CH$_3$). IR (neat): 3049, 3028, 2949, 2920, 2859, 1596, 1479, 1092, 1005, 811, 788, 747, 687 cm$^{-1}$. MS (EI) m/z (relative intensity): 320 ([M$^+$] 67), 201 (54), 166 (93), 91 (100), 65 (35). HR-MS (ESI) m/z calculated for C$_{20}$H$_{18}$ClN$_2$ [M+H$^+$] 321.1159, found 321.1141.

Example 22: (E)-1-(3',4'-Dichloro-4-methylbiphenyl-2-yl)-2-(3-methylphenyl)diazene

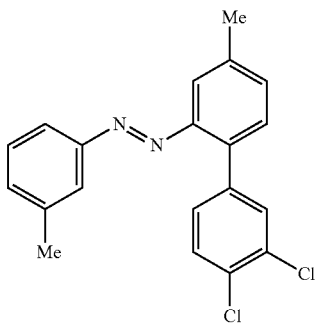 [SMILES: Cc1cccc(/N=N/c2cc(C)ccc2-c2ccc(Cl)c(Cl)c2)c1]

In an oven-dried reaction vessel, a suspension consisting of (E)-1,2-di-m-tolyldiazene (210 mg, 1.0 mmol), [{RuCl$_2$(p-cymene)}$_2$] (15.3 mg, 5.0 mol %), MesCO$_2$H (24.6 mg, 30 mol %), K$_2$CO$_3$ (138 mg, 1.0 mmol) and 4-bromo-1,2-dichlorobenzene (113 mg, 0.5 mmol) was stirred in dry 1,4-dioxane (2.0 ml) at 120° C. for 18 h in a nitrogen atmosphere. The reaction mixture was then diluted at 23° C. with CH$_2$Cl$_2$ (75 ml) and filtered through Celite and silica gel, and the filtrate was concentrated. The crude product thus obtained was purified by chromatography on silica gel (n-hexane/EtOAc/NEt$_3$: 88/6/6). (E)-1-(3',4'-Dichloro-4-methylbiphenyl-2-yl)-2-(3-methylphenyl)diazene (112 mg, 63%) was obtained as a pale orange solid. M.p.=127-128° C. $^1$H-NMR (CDCl$_3$, 500 MHz): δ=7.62-7.56 (m, 4H), 7.46 (d, J=8.3 Hz, 1H), 7.42 (d, J=7.8 Hz, 1H), 7.38-7.33 (m, 2H), 7.29-7.25 (m, 2H), 2.46 (s, 3H), 2.42 (s, 3H). $^{13}$C-NMR (CDCl$_3$, 126 MHz): δ=152.9 (C$_q$), 149.1 (C$_q$), 139.1 (C$_q$), 139.0 (C$_q$), 138.8 (C$_q$), 136.0 (C$_q$), 132.6 (CH), 131.9 (CH), 131.8 (CH), 131.7 (C$_q$), 131.3 (C$_q$), 130.2 (CH), 130.1 (CH), 129.4 (CH), 129.0 (CH), 123.7 (CH), 120.5 (CH), 116.2 (CH), 21.4 (CH$_3$), 21.2 (CH$_3$). IR (neat): 3026, 2918, 2858, 1601, 1463, 1371, 1133, 1027, 882, 826, 808, 686 cm$^{-1}$. MS (EI) m/z (relative intensity): 354 ([M$^+$] 55), 235 (43), 200 (62), 165 (61), 91 (100), 65 (36). HR-MS (EI) m/z calculated for C$_{20}$H$_{16}$Cl$_2$N$_2$ [M$^+$] 354.0691, found 354.0686.

Comparative Example 1: Methyl 4'-methyl-2'-[(E)-(3-methylphenyl)diazenyl]biphenyl-4-carboxylate The experiment was carried out as described for Example 1, with the difference that N,N-dimethylformamide was used as solvent in place of 1,4-dioxane. No target product was obtained.

Comparative Example 2: Methyl 4'-methyl-2'-[(E)-(3-methylphenyl)diazenyl]biphenyl-4-carboxylate The experiment was carried out as described for Example 1, with the difference that N,N-dimethylacetamide was used as solvent in place of 1,4-dioxane. No target product was obtained.

Comparative Example 3: Methyl 4'-methyl-2'-[(E)-(3-methylphenyl)diazenyl]biphenyl-4-carboxylate The experiment was carried out as described for Example 1, with the difference that methanol was used as solvent in place of 1,4-dioxane. No target product was obtained.

Comparative Example 4: Methyl 4'-methyl-2'-[(E)-(3-methylphenyl)diazenyl]biphenyl-4-carboxylate The experiment was carried out as described for Example 1, with the difference that N-methylpyrrolidone was used as solvent in place of 1,4-dioxane. No target product was obtained.

Comparative Example 5: Methyl 4'-methyl-2'-[(E)-(3-methylphenyl)diazenyl]biphenyl-4-carboxylate The experiment was carried out as described for Example 1, with the difference that γ-valerolactone was used as solvent in place of 1,4-dioxane. No target product was obtained.

Comparative Example 6: Methyl 4'-methyl-2'-[(E)-(3-methylphenyl)diazenyl]biphenyl-4-carboxylate The experiment was carried out as described for Example 1, with the difference that dimethyl sulphoxide was used as solvent in place of 1,4-dioxane. No target product was obtained.

Comparative Example 7: Methyl 4'-methyl-2'-[(E)-(3-methylphenyl)diazenyl]biphenyl-4-carboxylate The experiment was carried out as described for Example 1, with the difference that water was used as solvent in place of 1,4-dioxane. No target product was obtained.

Comparative Example 8: Methyl 4'-methyl-2'-[(E)-(3-methylphenyl)diazenyl]biphenyl-4-carboxylate The experiment was carried out as described for Example 1, with the difference that acetic acid was used as solvent in place of 1,4-dioxane. No target product was obtained.

Example 23: Methyl 2'-amino-4'-methylbiphenyl-4-carboxylate

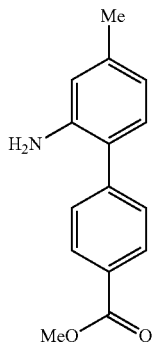

In an oven-dried reaction vessel, a suspension consisting of (E)-1,2-di-m-tolyldiazene (421 mg, 2.0 mmol), [{RuCl$_2$(p-cymene)}$_2$] (30.6 mg, 5.0 mol %), MesCO$_2$H (49.3 mg, 30 mol %), K$_2$CO$_3$ (276 mg, 2.0 mmol) and methyl 4-bromobenzoate (215 mg, 1.0 mmol) was stirred in dry 1,4-dioxane (3.0 ml) at 120° C. for 18 h in a nitrogen atmosphere. To the reaction mixture at 23° C. was then added [RuCl$_2$(PPh$_3$)$_3$] (47.9 mg, 5.0 mol %), KOH (16.8 mg, 30 mol %), Zn (262 mg, 4.0 mmol), H$_2$O (14.4 mg, 8.0 mmol) and finally 1,4-dioxane (2.0 ml). The mixture was stirred at 80° C. for 24 h in a nitrogen atmosphere. The reaction mixture was then diluted at 23° C. with EtOAc (75 ml) and filtered through Celite and silica gel, and the filtrate was concentrated. The crude product thus obtained was purified by chromatography on silica gel (n-hexane/EtOAc: 5/1). Methyl 2'-amino-4'-methylbiphenyl-4-carboxylate (160 mg, 66%) was obtained as a white solid.

M.p.=136-137° C. $^1$H-NMR (CDCl$_3$, 300 MHz): δ=8.08 (d, J=8.6 Hz, 2H), 7.52 (d, J=8.6 Hz, 2H), 7.02 (d, J=7.7 Hz, 1H), 6.65 (ddd, J=7.7, 1.6, 0.7 Hz, 1H), 6.59 (s, 1H), 3.92 (s, 3H), 3.71 (s, 2H), 2.30 (s, 3H). $^{13}$C-NMR (CDCl$_3$, 400 MHz): δ=166.9 (C$_q$), 144.5 (C$_q$), 143.2 (C$_q$), 139.2 (C$_q$), 130.2 (CH), 130.0 (CH), 129.0 (CH), 128.6 (C$_q$), 123.7 (C$_q$), 119.8 (CH), 116.5 (CH), 52.1 (CH$_3$), 21.2 (CH$_3$). IR (neat): 3442, 3360, 2947, 2915, 2164, 1703, 1604, 1435, 1280, 1178, 1103, 772 cm$^{-1}$. MS (EI) m/z (relative intensity): 241 ([M$^+$] 100), 210 (31), 167 (35), 84 (24), 49 (38). HR-MS (EI) m/z calculated for C$_1$H$_{15}$NO$_2$ [M$^+$] 241.1103, found 241.1109.

The invention claimed is:

1. Method for preparing a biphenylamine of formula (I)

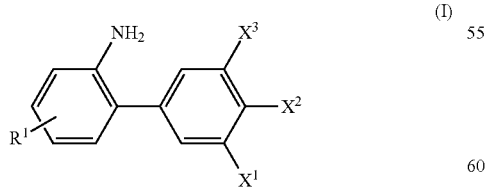

in which
R$^1$ is hydrogen, hydroxyl, fluorine, chlorine, C$_1$-C$_4$-alkyl, C$_1$-C$_4$-alkoxy, C$_1$-C$_4$-alkylthio or C$_1$-C$_4$-haloalkyl,
X$^1$ is hydrogen, alkoxy, alkanoyl, alkyl carboxylate, fluorine or chlorine,
X$^2$ is hydrogen, alkoxy, alkanoyl, alkyl carboxylate, fluorine or chlorine,
X$^3$ is hydrogen, alkoxy, alkanoyl, alkyl carboxylate, fluorine or chlorine,
comprising: (I) reacting one or more azobenzenes of formula (II)

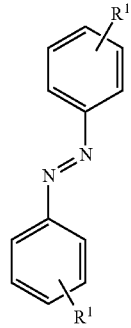

in which
R$^1$ is as defined above,
with an aromatic compound of formula (III)

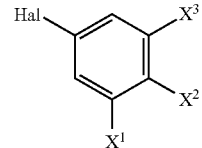

in which
X$^1$, X$^2$ and X$^3$ are each as defined above, and
Hal is iodine, bromine or chlorine
in the presence of a catalyst system consisting of a ruthenium catalyst, an activator, and a base, and (2) the azobenzenes of the formula (IV) thus obtained

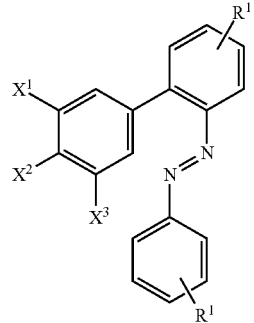

in which R$^1$, X$^1$, X$^2$ and X$^3$ are as defined above, are hydrogenated to give the biphenylamines of the formula (I).

2. Method according to claim 1, wherein the solvent comprises ketones, nitriles, ethers, hydrocarbons and halogenated hydrocarbons and branched alcohols and/or a mixture thereof.

3. Method according to claim 1, wherein the solvent comprises 1,4-dioxane, toluene, ortho-xylene, meta-xylene, para-xylene and/or a mixture thereof.

4. Method according to claim 1, wherein the catalyst is [{RuCl$_2$(p-cymene)}$_2$].

5. Method according to claim 1, wherein the activator is an acid, optionally a carboxylic acid.

6. Method according to claim 1, wherein the activator is a carboxylic acid selected from the group consisting of: formic acid, acetic acid, propionic acid, pivalic acid, benzoic acid, 2-methylbenzoic acid, 3-methylbenzoic acid, 4-methylbenzoic acid, 2,3-dimethylbenzoic acid, 2,4-dimethylbenzoic acid, 2,5-dimethylbenzoic acid, 2,6-dimethylbenzoic acid, 3,4-dimethylbenzoic acid, 3,5-dimethylbenzoic acid, 2,4,6-trimethylbenzoic acid, 2,3,4-trimethylbenzoic acid, 3,4,5-trimethylbenzoic acid, 2,3,5-trimethylbenzoic acid, 2,3,6-trimethylbenzoic acid, phenylacetic acid, 2-methylphenylacetic acid, 3-methylphenylacetic acid, 4-methylphenylacetic acid, 2,5-dimethylphenylacetic acid, 2,3,6-trimethylphenylacetic acid, 2,3,5,6-tetramethylphenylacetic acid, 2,3,4,6-tetramethylphenylacetic acid, 2-chlorophenylacetic acid, 3-chlorophenylacetic acid, 4-chlorophenylacetic acid and 2,4-dichlorophenylacetic acid.

7. Method according to claim 1, wherein the activator is 2,4,6-trimethylbenzoic acid.

8. Method according to claim 1, wherein the base is an inorganic base.

9. Method according to claim 1, wherein the base is selected from the group consisting of: lithium hydroxide, sodium hydroxide, potassium hydroxide, lithium carbonate, sodium carbonate, potassium carbonate, lithium hydrogen carbonate, sodium hydrogen carbonate, potassium hydrogen carbonate, calcium carbonate and magnesium carbonate.

10. Method according to claim 1, wherein the base is potassium carbonate.

11. Method according to claim 1, wherein the activator is used in an amount of 0.1 to 100 mole percent, based on the aromatic compound of the formula (III).

12. Method according to claim 1, wherein the ruthenium catalyst is used in an amount of 1 to 20 mole percent, based on the aromatic compound of the formula (III).

13. Method according to claim 1, wherein the molar ratio of azobenzene of the formula (II) to haloaromatic compound of the formula (III) is 1:0.4 to 1.

14. Method according to claim 1, wherein the molar ratio of azobenzene of the formula (II) to haloaromatic compound of the formula (III) is 1:0.45 to 0.9.

15. Method according to claim 1, wherein the solvent is 1,4-dioxane, the activator is 2,4,6-trimethylbenzoic acid, the aromatic compound of the formula (III) is a brominated aromatic compound, the base is potassium carbonate and the catalyst is [{RuCl$_2$(p-cymene)}$_2$].

* * * * *